United States Patent [19]

Tamburrino et al.

[11] Patent Number: 4,989,581
[45] Date of Patent: Feb. 5, 1991

[54] TORSIONAL STRAIN RELIEF FOR BORESCOPE

[75] Inventors: Richard A. Tamburrino, Auburn; Alan S. Knieriem, Syracuse, both of N.Y.

[73] Assignee: Welch Allyn, Inc., Skaneateles Falls, N.Y.

[21] Appl. No.: 531,557

[22] Filed: Jun. 1, 1990

[51] Int. Cl.$^5$ ............................................... A61B 1/00
[52] U.S. Cl. ......................................................... 128/4
[58] Field of Search ........................ 128/4, 6; 358/98

[56] References Cited

U.S. PATENT DOCUMENTS

| | | | |
|---|---|---|---|
| 3,583,393 | 6/1971 | Takahashi | 128/6 X |
| 3,610,231 | 10/1971 | Takahashi et al. | 128/6 |
| 3,669,098 | 6/1972 | Takahashi | 128/6 |
| 3,739,770 | 6/1973 | Mori | 238/6 |
| 3,799,751 | 3/1974 | Fukaumi et al. | 128/6 |
| 4,253,447 | 3/1981 | Moore et al. | 128/6 |
| 4,261,344 | 4/1981 | Moore et al. | 128/6 |
| 4,347,837 | 9/1982 | Hosono | 128/6 |
| 4,491,865 | 1/1985 | Danna et al. | 128/4 X |
| 4,532,918 | 8/1985 | Wheeler | 128/6 |
| 4,539,586 | 9/1985 | Danna et al. | 128/6 X |
| 4,546,379 | 10/1985 | Sarofeen et al. | 358/98 X |
| 4,621,618 | 11/1986 | Omagari | 128/6 |
| 4,700,693 | 10/1987 | Lia et al. | 128/4 |
| 4,794,912 | 1/1989 | Lia | 128/4 |

Primary Examiner—William H. Grieb
Attorney, Agent, or Firm—Wall and Roehrig

[57] ABSTRACT

A torsional strain relief assembly is provided for absorbing torsional strain at the proximal end of an elongated flexible insertion tube of a borescope or endoscope. The insertion tube is torsionally stiff, i.e. is bendable but resists rotation or twisting about its axis. The strain relief has a tubular rigid sleeve that is attached at its proximal end to a frame or housing, and contains a helical torsion spring whose proximal end is rotationally affixed to the frame. A bushing is rotatably disposed within the distal end of the sleeve and joins the distal end of the spring to the proximal end of the insertion tube. A layer of low friction material such as PTFE can be interposed between the bushing and the inner surface of the rigid sleeve. Rotation of the insertion tube due to bending and twisting is taken up by the spring, and the spring returns the insertion tube to the original position when the twisting forces are relieved. The oeprator can track the orientation of the optical or video imager in the head of the insertion tube by viewing a reference mark or index at the proximal end of the insertion tube.

7 Claims, 2 Drawing Sheets

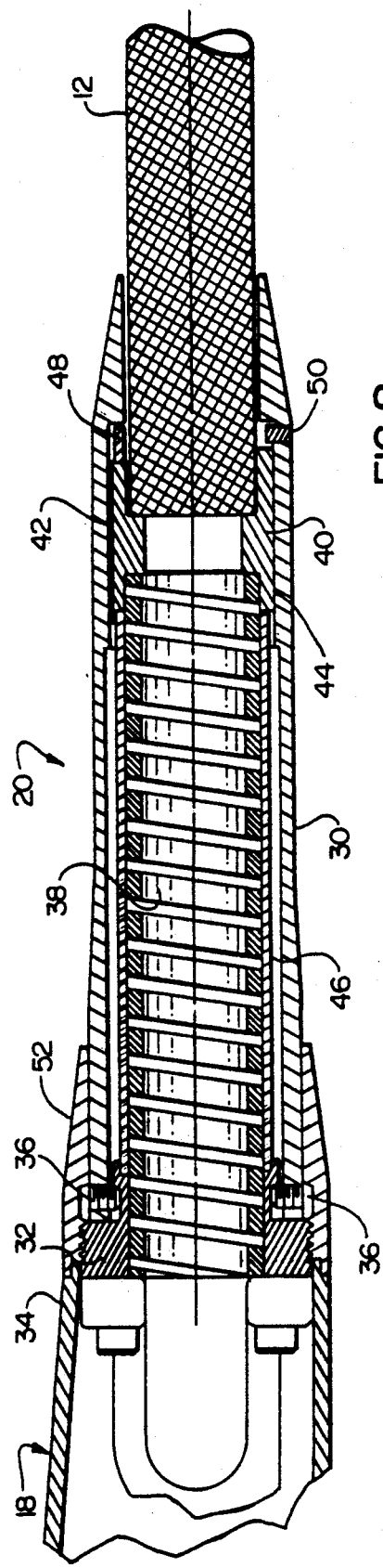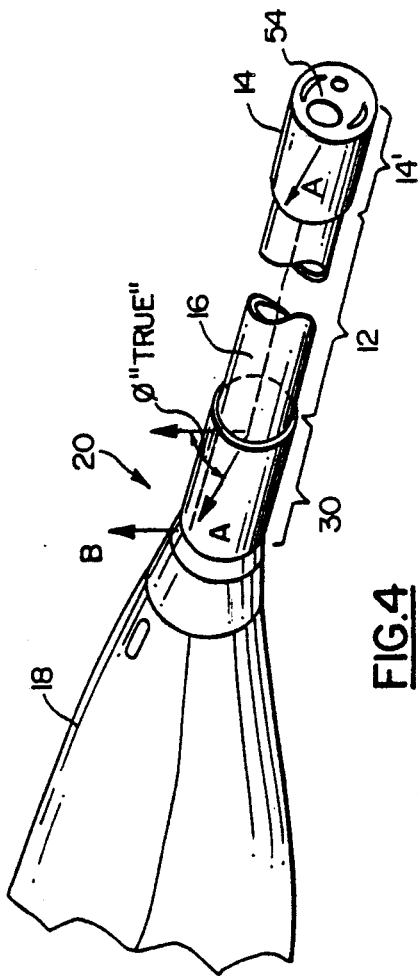

TORSIONAL STRAIN RELIEF FOR BORESCOPE

BACKGROUND OF THE INVENTION

This invention relates to elongated flexible probes, such as borescopes and endoscopes, and is more particularly directed to a torsional strain relief that absorbs torsional stress at the proximal end of a borescope or endoscope insertion tube.

A borescope is generally characterized as an elongated flexible insertion tube with a viewing head at its distal or forward end, and a control section at its proximal end for controlling the bending at the distal end. In such a borescope, a bendable tube steering section is situated at the distal end adjacent to the viewing head. Typically, control cables extend through the bendable tube section and the remainder of the insertion tube and connect with a steering control mechanism in the control section. These cables are differentially displaced for bending the steering section to facilitate the inspection of a remote object.

A borescope is typically intended for visual inspection of an intricate mechanical assembly, such as a jet engine or turbine, or a heat exchanger tube, where it would be difficult or impossible otherwise to view the assembly's internal elements. The borescope needs to be insertable into narrow, tortuous passageways, and must observe very delicate steering considerations. It often occurs, because of the many bends that the insertion tube must undergo, that a torsion or twisting force is applied onto the insertion tube, which can produce a rotational strain at the junction of the insertion tube with the control section.

An endoscope is typically inserted into a body cavity of a human or veterinary patient for visual inspection of tissues within the cavity. Because body passages such as esophagus, bronchi, and colon are narrow and tortuous, the steering section must be bent rather precisely, and as close to the viewing head as possible. Thus, cable tension must be limited and cable slack minimized as much as possible. In many types of diagnosis or treatment, such as in the colon or the small intestine, the probe insertion tube is subjected to a large number of bends. These can impose a twisting force on the insertion tube.

In either type of probe, the twisting of the insertion tube can produce a loss of alignment of the viewing head, and the degree and direction of misalignment is difficult or impossible to estimate.

Currently, insertion tubes are of a torsionally stiff design, and although they will bend, they are not free to rotate about their own axis. Accordingly, if this type of insertion tube is forced to twist, the force will be absorbed at the weakest point, i.e. the junction of the proximal end of the insertion tube with the control section housing or frame. This can cause delamination of the insertion tube, particularly in an outer braid layer.

Borescopes and/or endoscopes of this general type are described in various U.S. Patents, e.g., U.S. Pat. Nos. 4,253,447; 4,261,344; 4,491,865. A similar type of probe is shown in U.S. Pat. No. 4,621,618 to Omagari. Further examples are described in U.S. Pat. Nos. 4,546,379; 4,523,224; 4,532,918, and 4,539,586. Various steering mechanisms for articulated, elongated flexible probes are described, e.g. in U.S. Pat. Nos. 3,610,231; 3,739,770; 3,593,393; 3,669,098; 3,779,151; 4,347,837 and 4,700,693. An alternative arrangement is described in U.S. Pat. No. 4,794,912. A review of this patent literature will provide a general background and understanding of borescopes, endoscopes, and similar probes.

OBJECTS AND SUMMARY OF THE INVENTION

It is an object of this invention to provide a strain relief assembly for a borescope or endoscope which can absorb the rotational or torsional stresses imposed on the insertion tube and thus avoid the drawbacks of the prior art.

It is another object of the invention to prevent delamination of the insertion tube, and thereby prolong its useful life.

It is a further object of this invention to provide a borescope or endoscope strain relief which permits an operator to maintain the vertical orientation of the probe even under conditions that induce torsional rotation of the probe insertion tube.

According to an aspect of the invention, a torsional strain relief assembly is provided for absorbing the torsional strain at the proximal end of an elongated flexible insertion tube and mechanically coupling the insertion tube to a frame, e.g., in the control section. The insertion tube is of the type that is bendable in one or two planes, but is torsionally stiff.

In a preferred embodiment, the strain relief assembly has a tubular rigid sleeve that is rigidly attached at its proximal end to the frame, and a helical torsion spring situated within the sleeve. The proximal end of the spring is rotationally affixed to the frame. A bushing is disposed within the distal end of the sleeve and is free to rotate within it. The bushing joins the distal end of the spring to the proximal end of the insertion tube.

A layer of PTFE (TEFLON) or another low, friction material can be interposed between the outer wall of the bushing and the inner surface of the rigid sleeve. This permits the proximal end of the insertion tube to rotate over a substantial angle, i.e. 180 degrees, with respect to the rigid sleeve and the frame. This rotation is taken up by the spring, which returns the insertion tube to its original position when the twisting forces are relieved.

An index stripe can be oriented on the insertion tube sheath to indicate the vertical position of the viewing head. With the stripe, the operator can orient the insertion tube so that the vertical sense Of the target object corresponds with the vertical sense of the image that appears on a viewer or screen at the proximal end of the probe. Where the insertion tube is of the type having a torsionally stiff sheath and a torsional strain relief, the index stripe at the proximal end of the insertion tube will indicate the true orientation of the viewing head at the distal tip.

In a preferred embodiment, the helical spring comprises a coil of three turns or more so as to absorb the rotational torque smoothly over an angle of up to 180 degrees. The coil thread or worm can have a rectangular cross section. An elastomeric sleeve, e.g. of shrink tubing, can be disposed over the spring.

A stop member can be disposed in the distal end of the tubular rigid sleeve to cooperate with a stop member on the bushing to limit the rotation to a predetermined amount, e.g. ±180° from the original or rest position.

The above and many other objects, features, and advantages of this invention will be understood from the ensuing detailed description of a preferred embodiment, to be read in connection with the accompanying Drawing.

BRIEF DESCRIPTION OF THE DRAWING

FIG. 2 is a cross section of the strain relief invention of this embodiment.

FIG. 4 is a simplified schematic view of a borescope according to a preferred embodiment of this invention.

DETAILED DESCRIPTION OF THE PREFERRED EMBODIMENT

Figure 1:
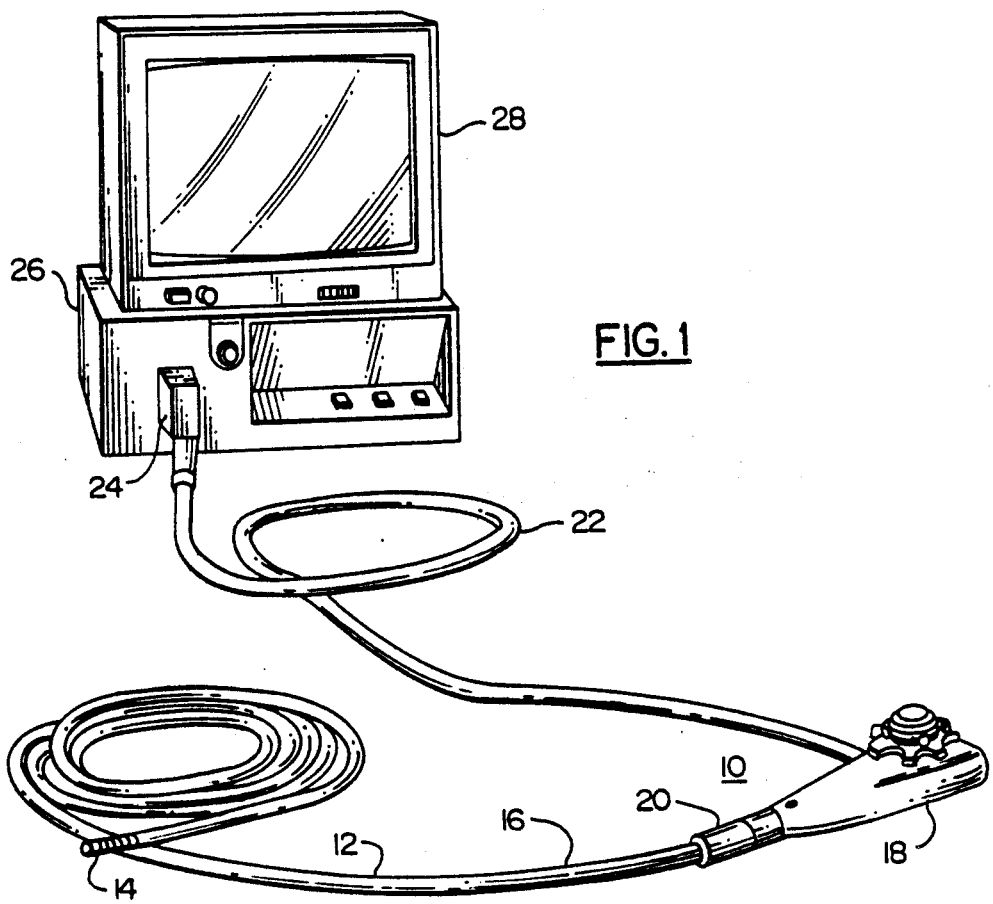
FIG. 1 is a perspective view of a borescope that has a torsional strain relief assembly according to one preferred embodiment of this invention.

With reference to the Drawing, and initially to FIG. 1, an endoscope or borescope 10, which is an elongated optical or video probe, comprises an elongated flexible insertion tube 12 which has a tubular, tortionally stiff outer sheath. At a distal tip of the insertion tube 12 is a viewing head 14, in this case of the type employing a video imager. In other embodiments, the viewing head 14 can be of the optical type in which an image is focused onto a fiber optic bundle which carries it to a viewing device. An index stripe 16 runs along an upper surface of the tube 12 to indicate the vertical or up-and-down imaging direction of the viewing head 14.

A control unit 18 is provided for steering the bending section which is disposed at the distal tip of the insertion tube. The control unit 18 is joined to the insertion tube 12 by means of a torsional strain relief assembly 20.

From the control unit 18, an umbilical 22 carries communication and signal conduits, as well as a fiber optic illumination bundle, between the control unit and a modular connector 24 that fits a receptacle in a video processor 26. A viewing screen 28 on the processor 26 reproduces an image of a target as viewed by a viewing head 14.

As shown in FIG. 2, the torsional strain relief assembly 20 comprises a tubular rigid sleeve 30 whose proximal end is seated on a fitting or coupler 32 disposed at the distal end of a frame 34 of the control unit 18. Several screws 36 are distributed over the periphery of the proximal end of the sleeve 30. These screws hold the sleeve 30 to the fitting 32, and can be loosened to permit rotational adjustment.

A coil torsion spring 38 is positioned axially within the sleeve 30 and has its proximal end affixed to the fitting 32. The torsion spring 38 has a thread or worm of generally rectangular cross section, and consists of a sufficient number of turns, i.e. at least three turns, so that a substantial rotation of the insertion tube 12 can be absorbed smoothly by the spring 38. Alteratively, the thread or worm could be of round cross section. A rotary bushing 40 is situated within the distal end of the sleeve 30, and attaches the distal end of the spring 38 to the proximal end of the insertion tube 12. On an outer cylindrical surface of the bushing 40 of this embodiment, there is a layer 42 of polytetrafluoroethylene (TEFLON) or another suitable low-friction material to ensure low friction contact with a mating inner cylindrical surface 44 at the distal end of the tubular rigid sleeve 30.

A sleeve 46 of an elastomeric material 46 covers the spring 38. The sleeve 46 can be shrink fit over the spring.

A stop lug 48 projects from the distal end of the bushing 40, and a corresponding stop lug 50 extends radially into the sleeve 30 adjacent the distal end of the bushing 40. These two stop lugs 48 and 50 serve to limit rotation of the bushing 40 and the attached insertion tube 12 to an angle of approximately 180 degrees to either side of a rest position.

As also shown, a cover ring 52 has internal threads and is screwed onto the fitting 32 to cover the proximal end of the rigid sleeve 30.

Figure 3:
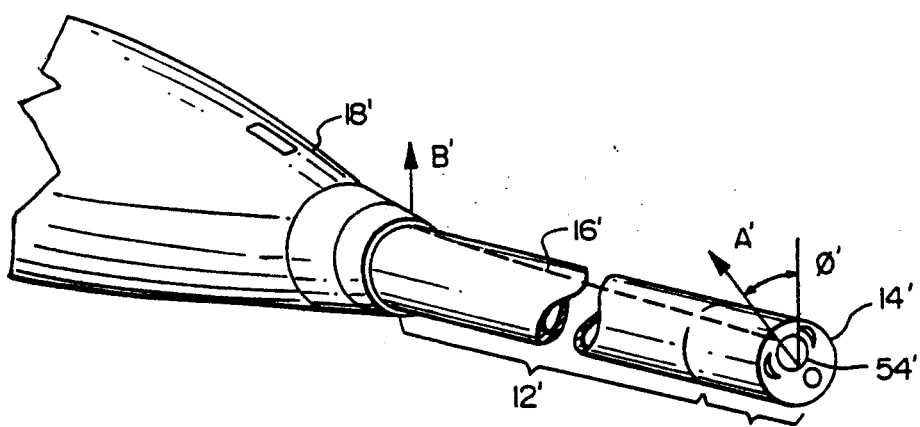
FIG. 3 is a simplified schematic view of a borescope of conventional construction.

The advantages of this invention can be explained with reference to FIGS. 3 and 4. FIG. 3 is a simplified view of a borescope of conventional construction, in which the elements that correspond with those of this invention are identified with the same reference numbers, but primed. In this borescope there is a conventional insertion tube 12' which is tortionally flexible so that strain from twisting is distributed over the length of the insertion tube 12'. An index mark or stripe 16' twists with the torsional strain of the insertion tube 12' from the viewing head 14' to the control unit 18'. In this borescope there is a video imager unit 54' situated within the viewing head 14'. An arrow A' indicates the vertical direction in respect to the imager unit 54'. Another arrow B' at the control section 18' i.e. at the proximal end of the insertion tube 12' indicates the true vertical direction as indicated at the proximal end of the index stripe 16'. Due to twisting and torsional stresses on the insertion tube 12' there is an error angle $\theta'$ between the imager vertical and true vertical directions, and this error angle $\theta'$ is of unknown magnitude and direction.

FIG. 4 is a simplified view of the borescope of the present invention, in which the insertion tube 12 is torsionally stiff, as previously mentioned. Here, the imager vertical direction is as indicated by an arrow A. Rotation of the viewing head 14, when displaced from true vertical, is carried to the index stripe 16 that appears at the proximal end of the tube 12. The error angle $\theta$ that appears between the imager vertical direction and the true or control section vertical direction, as indicated by an arrow B, is readily apparent to the operator, both in magnitude and direction. The torsional strain relief assembly 20 absorbs the torsional forces at the proximal end of insertion tube 12 and prevents wear of the insertion tube sheath thereby prolonging its useful life.

The strain relief assembly 20 constructed according to the principles of this invention can be employed with insertion tubes with any of various dimensions, including e.g. the 10 mm and 12.7 mm diameter borescopes that are in common usage. The torsional strain relief assembly 20 allows rotation of the insertion tube 12 without the borescope operator losing his or her frame of reference and without damage to the insertion tube.

While this invention has been described in detail with respect to a preferred embodiment, it should be understood that the invention is not limited to that precise embodiment; rather many modifications and variations will present themselves to those with skill in the art without departing from the scope and spirit of this invention, as defined in the appended claims.

What is claimed is:

1. Torsional strain relief assembly for absorbing torsional strain at a proximal end of an elongated, flexible insertion tube of a borescope or endoscope and for mechanically coupling the insertion tube to a frame, said strain relief assembly comprising a tubular rigid sleeve; means rigidly affixing a proximal end of the tubular rigid sleeve to said frame; a helical torsional spring situated within said tubular rigid sleeve; means rotationally affixing a proximal end of said spring to said frame; a bushing rotationally affixed to a distal end of said spring and to a proximal end of said insertion tube and rotatably mounted within said rigid tubular sleeve, permitting rotation of said insertion tube over at least a substantial rotational angle with respect to said rigid sleeve and said frame; such that said insertion tube is free to rotate over said substantial angle without significant twisting over the length of the insertion tube.

2. Torsional strain relief assembly according to claim 1, wherein said insertion tube has a torsionally stiff tubular sheath that is substantially constrained from twisting about its own axis.

3. Torsional strain relief assembly according to claim 1 wherein said insertion tube bears an index mark on its outer surface at least at its proximal end to indicate orientation of its distal end.

4. Torsional strain relief assembly according to claim 1 wherein said helical spring comprises at least three turns.

5. Torsional strain relief assembly according to claim 1 wherein said helical spring has a worm of rectangular cross section.

6. Torsional strain relief assembly according to claim 1 further comprising an elastomeric sleeve disposed on a radial outer surface of said spring.

7. Torsional strain relief assembly according to claim 1, further comprising stop means disposed in the distal end of said tubular rigid sleeve and cooperating means in said bushing to block mutual rotation of about one-half rotation either direction from a central rest position.

* * * * *